United States Patent
Douglas et al.

(10) Patent No.: US 12,333,087 B2
(45) Date of Patent: Jun. 17, 2025

(54) INTERACTIVE 3D CURSOR

(71) Applicant: D3D Technologies, Inc., Orlando, FL (US)

(72) Inventors: Kathleen M. Douglas, Winter Park, FL (US); Robert E. Douglas, Winter Park, FL (US); David Byron Douglas, Winter Park, FL (US)

(73) Assignee: D3D Technologies, Inc., Orlando, FL (US)

( * ) Notice: Subject to any disclaimer, the term of this patent is extended or adjusted under 35 U.S.C. 154(b) by 0 days.

(21) Appl. No.: 18/047,256

(22) Filed: Oct. 17, 2022

(65) Prior Publication Data

US 2023/0341952 A1     Oct. 26, 2023

Related U.S. Application Data

(63) Continuation of application No. 17/339,341, filed on Jun. 4, 2021, now Pat. No. 11,520,415, which is a
(Continued)

(51) Int. Cl.
*G06F 3/0346* (2013.01)
*A61B 5/00* (2006.01)
(Continued)

(52) U.S. Cl.
CPC ............ *G06F 3/0346* (2013.01); *A61B 5/489* (2013.01); *A61B 6/466* (2013.01);
(Continued)

(58) Field of Classification Search
CPC ............... G06F 3/0346; G06F 3/03543; G06F 3/04812; G06F 3/04815; G06F 3/04842;
(Continued)

(56) References Cited

U.S. PATENT DOCUMENTS 5,371,778 A * 12/1994 Yanof ................. G06F 3/04845
378/4
5,488,952 A     2/1996 Schoolman
(Continued)

FOREIGN PATENT DOCUMENTS

WO     2007059477 A2     5/2007

OTHER PUBLICATIONS

IPR2021-00647 Final Written Decision in *Microsoft Corporation v. D3D Technologies, Inc.*; United States Patent and Trademark Office—Before the Patent Trial and Appeal Board, Case No. IPR2021-00647; Entered Aug. 3, 2022 (31 pages).
(Continued)

*Primary Examiner* — Robin J Mishler
(74) *Attorney, Agent, or Firm* — Almanac IP Advisors LLP

(57) ABSTRACT

An interactive 3D cursor facilitates selection and manipulation of a three-dimensional volume from a three-dimensional image. The selected volume image may be transparency-adjusted and filtered to remove selected tissues from view. Qualitative and quantitative analysis of tissues in a selected volume may be performed. Location indicators, annotations, and registration markers may be overlaid on selected volume images.

30 Claims, 16 Drawing Sheets

Related U.S. Application Data continuation of application No. 17/122,518, filed on Dec. 15, 2020, now Pat. No. 11,036,311, which is a continuation of application No. 17/021,548, filed on Sep. 15, 2020, now Pat. No. 10,936,090, which is a continuation of application No. 15/878,463, filed on Jan. 24, 2018, now Pat. No. 10,795,457.

(51) Int. Cl.

| | | |
|---|---|---|
| *A61B 6/46* | (2024.01) | |
| *G06F 3/0354* | (2013.01) | |
| *G06F 3/04812* | (2022.01) | |
| *G06F 3/04842* | (2022.01) | |
| *G06T 7/00* | (2017.01) | |
| *G06T 7/62* | (2017.01) | |
| *G06T 19/00* | (2011.01) | |
| *H04N 13/183* | (2018.01) | |
| *H04N 13/344* | (2018.01) | |

(52) U.S. Cl.
CPC ...... *G06F 3/03543* (2013.01); *G06F 3/04812* (2013.01); *G06F 3/04842* (2013.01); *G06T 7/0012* (2013.01); *G06T 7/0014* (2013.01); *G06T 7/62* (2017.01); *G06T 19/00* (2013.01); *G06T 19/006* (2013.01); *H04N 13/183* (2018.05); *H04N 13/344* (2018.05); *G06T 2207/10072* (2013.01); *G06T 2207/10081* (2013.01); *G06T 2207/10104* (2013.01); *G06T 2207/20104* (2013.01); *G06T 2207/30096* (2013.01); *G06T 2207/30204* (2013.01); *G06T 2210/41* (2013.01)

(58) Field of Classification Search
CPC ......... A61B 5/489; A61B 6/466; G06T 19/00; G06T 19/006; G06T 2207/10072; G06T 2207/10081; G06T 2207/10104; G06T 2207/20104; G06T 2207/30096; G06T 2207/30204; G06T 2210/41; G06T 7/0012; G06T 7/0014; G06T 7/62; H04N 13/183; H04N 13/344
See application file for complete search history.

(56) References Cited

U.S. PATENT DOCUMENTS

| | | | |
|---|---|---|---|
| 6,692,441 B1* | 2/2004 | Poland ............. | G06T 15/08 600/443 |
| 8,384,771 B1 | 2/2013 | Douglas | |
| 9,600,929 B1* | 3/2017 | Young ............. | G06T 17/00 |
| 10,795,457 B2 | 10/2020 | Douglas et al. | |
| 2003/0142144 A1* | 7/2003 | Balakrishnan ...... | G06F 3/033 715/848 |
| 2012/0306849 A1* | 12/2012 | Steen ............. | G06F 3/04812 345/419 |
| 2013/0245375 A1 | 9/2013 | DiMaio et al. | |
| 2016/0246923 A1 | 8/2016 | Rooyen et al. | |
| 2018/0232951 A1* | 8/2018 | Alterovitz ......... | A61B 34/30 |

OTHER PUBLICATIONS

IPR2021-00647 Petition for Inter Partes Review of U.S. Pat. No. 8,384,771 Pursuant to 35 U.S.C. §§ 311-319, 37 C.F.R. § 42; United States Patent and Trademark Office—Before the Patent Trial and Appeal Board, Case No. IPR2021-00647, filed Mar. 23, 2021 (112 pages).
IPR2021-00647 Petitioner's Reply to Patent Owner's Response in *Microsoft Corporation v. D3D Technologies, Inc.*; United States Patent and Trademark Office—Before the Patent Trial and Appeal Board, Case No. IPR2021-00647; Entered on Feb. 23, 2022 (29 pages).
IPR2021-01325 Final Written Decision Determining Some Challenged Claim Unpatentable in *Microsoft Corporation v. D3D Technologies, Inc.*; United States Patent and Trademark Office—Before the Patent Trial and Appeal Board, Case No. IPR2021-01325; Entered Feb. 13, 2023 (75 pages).
IPR2021-01325 Petition for Inter Partes Review of U.S. Pat. No. 10,795,457 Pursuant to 35 U.S.C. §§ 311-319, 37 C.F.R. § 42; United States Patent and Trademark Office—Before the Patent Trial and Appeal Board, Case No. IPR2021-01325, filed Aug. 25, 2021 (120 pages).
IPR2021-01325 Petitioner's Reply to Patent Owner's Response in *Microsoft Corporation v. D3D Technologies, Inc.*; United States Patent and Trademark Office—Before the Patent Trial and Appeal Board, Case No. IPR2021-01325; Entered Sep. 9, 2022 (40 pages).
Non-Final Office Action mailed Dec. 19, 2023 in U.S. Appl. No. 18/049,272 (193 pages).
Reissue U.S. Appl. No. 18/049,272, filed Oct. 24, 2022 (100 pages).
United States Court of Appeals for the Federal Circuit; Case No. 23-1011; Appeal from the United States Patent and Trademark Office, Patent Trial and Appeal Board in No. IPR2021-00647; *Microsoft Corporation v. D3D Technologies, Inc.*; Decided Feb. 20, 2024 (8 pages).
United States Court of Appeals for the Federal Circuit; Case No. 23-1462; Appeal from the United States Patent and Trademark Office, Patent Trial and Appeal Board in No. IPR2021-00878; *D3D Technologies, Inc. v. Microsoft Corporation*; Decided Apr. 3, 2024 (11 pages).
Defendant Microsoft Corporation's Fifth Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Jan. 10, 2022 (23 Pages).
Defendant Microsoft Corporation's Fourth Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Nov. 15, 2021 (52 Pages).
Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (158 Pages).
Defendant Microsoft Corporation's Second Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Sep. 17, 2021 (14 Pages).
Defendant Microsoft Corporation's Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Apr. 19, 2021 (5 Pages).
Defendant Microsoft Corporation's Third Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Oct. 12, 2021 (17 Pages).
Exhibit A: "Moreira DA, Hage C, Luque Ef, "3D Markup of Radiological Images in ePAD, A Web-Based Image Annotation Tool," 2015 IEEE 28th International Symposium on Computer-Based Medical Systems, 97-102 (2015)" from Defendant Microsoft Corporation's Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Apr. 19, 2021 (6 pages).
Exhibit A-1: "U.S. Pat. No. 8,384,771 Invalidity Chart Based On The 3D Slicer Prior Art System" from Defendant Microsoft Corporation's Fifth Supplemental Invalidity Contentions for *D3D Technologies. Inc. v. Microsoft Corporation*; U.S. District Court, Middle District of Florida Orlando Division; Case No. 6:20-cv-1699-PGB-DCI; 125 pages.

(56) References Cited

OTHER PUBLICATIONS

Exhibit A-1: "U.S. Pat. No. 8,384,771 Invalidity Chart Based On The 3D Slicer Prior Art System" from Defendant Microsoft Corporation's Fourth Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Nov. 15, 2021 (96 Pages).
Exhibit A-1: "U.S. Pat. No. 8,384,771 Invalidity Chart Based On the OSIRIX 2005 System" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (120 pages).
Exhibit A-1: "U.S. Pat. No. 8,384,771 Invalidity Chart Based On The Siemens 3D Prior Art System" from Defendant Microsoft Corporation's Third Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Oct. 12, 2021 (72 Pages).
Exhibit A-13: "U.S. Patent No. 9,349, 183 is Anticipated By and/or Rendered Obvious In View of Bauch" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (112 Pages).
Exhibit A-2: "U.S. Pat. No. 8,384,771 is Anticipated By and/or Rendered Obvious In View of Kniss" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (126 Pages).
Exhibit A-3: "U.S. Pat. No. 8,384,771 is Anticipated By and/or Rendered Obvious In View of Lima" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (133 Pages).
Exhibit A-4: "U.S. Pat. No. 8,384,771 is Anticipated By and/or Rendered Obvious In View of Tooyama" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (115 Pages).
Exhibit A-6: "U.S. Pat. No. 8,384,771 is Anticipated By and/or Rendered Obvious In View of Kratz" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (106 Pages).
Exhibit A-7: "U.S. Pat. No. 8,384,771 is Anticipated By and/or Rendered Obvious In View of Schoolman '952" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (164 Pages).
Exhibit A-8: "U.S. Pat. No. 9,349,183 is Anticipated By and/or Rendered Obvious In View of Schoolman '595" from Defendant Microsoft Corporation's Preliminary Invalidity Contentions for *D3D Technologies. Inc. v. Microsoft Corporation*; U.S. District Court, Middle District of Florida Orlando Division; Case No. 6:20-cv-1699-GAP-DCI; Entered Feb. 4, 2021 (216 Pages).
Exhibit B: "U.S. Pat. No. 9,980,691 is Anticipated By and/or Rendered Obvious In View of Moreira" from Defendant Microsoft Corporation's Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Apr. 19, 2021 (68 pages).
Exhibit B-1: "International Application No. PCT/US2007/074689 to Anderson et al., filed on Jul. 30, 2007 ("Anderson")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Sep. 17, 2021 (18 pages).
Exhibit B-1: "U.S. Pat. No. 8,384,771 Invalidity Chart Based On the OSIRIX 2005 System" from Defendant Microsoft Corporation's Fifth Supplemental Invalidity Contentions for *D3D Technologies. Inc. v. Microsoft Corporation*; U.S. District Court, Middle District of Florida Orlando Division; Case No. 6:20-cv-1699-PGB-DCI; 123 pages.
Exhibit B-10: "U.S. Patent Publication No. 2004/0238732 A1 to State et al., issued May 11, 2010 ("State")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20- CV-1699-PGB-DCI; Entered Sep. 17, 2021 (32 pages).
Exhibit B-2: "Ronald T. Azuma, "A Survey of Augmented Reality" In Presence: Teleoperators and Virtual Environments 6, 4 (Aug. 1997) ("Azuma")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (48 pages).
Exhibit B-3: "Siemens, Operating Instructions, InSpace3Dflash, Neurostar/Angiostar/Multistar T.O.P./ Plus" from Defendant Microsoft Corporation's Third Supplemental Invalidity Contentions for *D3D Technologies. Inc. v. Microsoft Corporation*; U.S. District Court, Middle District of Florida Orlando Division; Case No. 6:20- cv-1699-PGB-DCI; Entered Oct. 12, 2021 (77 Pages).
Exhibit B-4: "Siemens, SCT and MR Workstation, The Power To See It All, 3DVirtuoso" from Defendant Microsoft Corporation's Third Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Oct. 12, 2021 (9 Pages).
Exhibit B-5: "Siemens, 510(k) Summary, Siemens Realtime 3D Software Package" from Defendant Microsoft Corporation's Third Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Oct. 12, 2021 (5 Pages).
Exhibit B-7: "OsiriX User Manual The Complete Reference, Revision 5.0.0 (Last Updated Apr. 24, 2017) ("User Manual")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (345 pages).
Exhibit B-8: "OsiriX Quick Manual, Version 1.0 ("Quick Manual")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (28 pages).
Exhibit B-9: "Antoine Rosset, MD et al., "OsiriX: An Open-Source Software for Navigating in Multidimensional DICOM Images" (Sep. 2004) ("Rosset")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (12 pages).
Exhibit C: "U.S. Pat. No. 10,795,457 Is Anticipated By and/or Rendered Obvious In View of Moreira" from Defendant Microsoft Corporation's Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Apr. 19, 2021 (64 pages).
Exhibit C-1: "U.S. Pat. No. 8,384,771 Invalidity Chart Based On the Siemens 3D Prior Art System" from Defendant Microsoft Corporation's Fifth Supplemental Invalidity Contentions for *D3D Technologies. Inc. v. Microsoft Corporation*; U.S. District Court, Middle District of Florida Orlando Division; Case No. 6:20-cv-1699-PGB-DCI; 178 pages.

(56) References Cited

OTHER PUBLICATIONS

Exhibit C-1: "U.S. Pat. No. 8,384,771 is Anticipated By and/or Rendered Obvious In View of the VIEW system" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-CV-1699-PGB-DCI; Entered Oct. 12, 2021 (101 Pages).

Exhibit D-1: "S.S. Fisher, et al., Virtual Environment Display System, Proceedings of the 1986 workshop on Interactive 3D graphics, Jan. 1987, at 77, https://doi.org/10.1145/319120.319127" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (12 Pages).

Exhibit D-10: "Scott Fisher, Telepresence in Dataspace NASA Ames VIEWlab, 1987, https://youtu.be/guOUfhoNhDY. ("1987 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.

Exhibit D-11: "Scott Fisher, NASA Ames VIEWlab VR demo reel 1989, https://youtu.be/3LON7CKvOBA ("1989 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20- CV-1699-PGB-DCI; Entered Oct. 12, 2021.

Exhibit D-12: "ACM SIGCHI, View: The Ames Virtual Environment Workstation, https://youtu.be/HOE16KLnnSE ("1990 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20- CV-1699-PGB-DCI; Entered Oct. 12, 2021.

Exhibit D-2: "S.S. Fisher, E.M. Wenzel, C. Coler, M.W. McGreevy, Virtual Interface Environment Workstations, 32 Proc. Hum. Factors Soc'y Ann. Meeting, Feb. 1988, at 91, http://doi.org/10.1177/154193128803200219" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20- CV-1699-PGB-DCI; Entered Oct. 12, 2021 (7 Pages).

Exhibit D-3: "A New Continent of Ideas, Spinoff 1990, Jan. 1, 1990, at 88, https://ntrs.nasa.gov/citations/20020086961" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-CV-1699-PGB-DCI; Entered Oct. 12, 2021 (5 Pages).

Exhibit D-4: "Scott S. Fisher, Virtual Environments, Personal Simulation & Telepresence, in Virtual Reality: Theory, Practice and Promise (S. Helsel and J.Roth, ed., Meckler Publishing, 1991)" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (8 Pages).

Exhibit D-5: "Steven D. Pieper et al., A Virtual Environment System for Simulation of Leg Surgery, Proc. SPIE 1457, Stereoscopic Displays and Applications II, Aug. 1, 1991, at 188, https://doi.org/10.1117/12.46307 ("Pieper 1991")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20- cv-1699-PGB-DCI; Entered Oct. 12, 2021 (12 Pages).

Exhibit D-6: "Richard H. Jacoby and Stephen R. Ellis, Using Virtual Menus in a Virtual Environment, Proc. SPIE 1668, Visual Data Interpretation, (Jun. 1, 1992); https://doi.org/10.1117/12.59654 ("Jacoby 1992")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (11 Pages).

Exhibit D-7: "Stephen R. Ellis, What Are Virtual Environments, 14 IEEE Computer Graphics & Applications, Jan. 1994, at 17, https://doi.org/10.1109/38.250914 ("Ellis 1994")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (7 Pages).

Exhibit D-8: "Scott S. Fisher, The NASA Ames VIEWlab Project-A Brief History, 25 Presence 339 (2016), https://doi. org/10.1162/PRES_a_00277 ("Fisher 2016")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (11 Pages).

Exhibit D-9: "MDx media, NASA Ames—virtual environment display system, NASA's research into VR from the 1980s, https://youtu.be/gd6_eojjTMU ("1985 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.

Final Office Action mailed Aug. 23, 2024 in U.S. Appl. No. 18/049,272 (78 pages).

\* cited by examiner

INTERACTIVE 3D CURSOR

RELATED APPLICATIONS

This application is a continuation of U.S. patent application Ser. No. 17/339,341 filed on Jun. 4, 2021, now U.S. Pat. No. 11,520,415, which is a continuation of U.S. patent application Ser. No. 17/122, 518, filed Dec. 15, 2020, now U.S. Pat. No. 11,036,311,which is a continuation of Ser. No. 17/021,548, filed Sep. 15, 2020, now U.S. Pat. No. 10,936, 090, which is a continuation of U.S. patent application Ser. No. 15/878,463, filed Jan. 24, 2018, now U.S. Pat. No. 10,795,457.

TECHNICAL FIELD

Aspects of this disclosure are generally related to human-machine interfaces, and more particularly to cursors.

BACKGROUND

The typical arrow-shaped cursor presented by a computer operating system is zero-dimensional. A zero-dimensional cursor designates the location of a single point in a space such as a two-dimensional window presented on a monitor. Mouse buttons can be used in combination with movement of the cursor to select objects in the two-dimensional space, but at any given instant of time a zero-dimensional cursor position designates only a single point in space.

The current standard for diagnostic radiologists reviewing computed tomography (CT) or magnetic resonance imaging (MRI) studies is a slice-by-slice method. A conventional keyboard, monitor, and mouse with a zero-dimensional cursor are used for manipulating the images. The use of mouse buttons and cursor movement for manipulating the images can become burdensome. For example, many images are included in radiology studies that are performed for the follow up of cancer to determine the response to treatment. The ability to recognize and analyze differences between images can be important. As an example, the recent Investigation of Serial Studies to Predict Your Therapeutic Response with Imaging and Molecular Analysis (I-SPY) trial tracked the changes in the tumor over multiple magnetic resonance imaging (MRI) scans during the administration of neoadjuvant chemotherapy (NACT). It has been noted that the phenotypic appearance (e.g., shape, margins) of a tumor correlated with the pathologic response to NACT. A more efficient and accurate interface for manipulating and presenting medical images would therefore have utility.

Known techniques for 3D viewing of medical images are described in U.S. Pat. No. 9,349,183, Method and Apparatus for Three Dimensional Viewing of Images, issued to Douglas, U.S. Pat. No. 8,384,771, Method and Apparatus for Three Dimensional Viewing of Images, issued to Douglas, Douglas, D. B., Petricoin, E. F., Liotta L., Wilson, E. D3D augmented reality imaging system: proof of concept in mammography. *Med Devices* (Auckl), 2016; 9:277-83, Douglas, D. B., Boone, J. M., Petricoin, E., Liotta, L., Wilson, E. Augmented Reality Imaging System: 3D Viewing of a Breast Cancer. *J Nat Sci.* 2016; 2(9), and Douglas, D. B., Wilke, C. A., Gibson, J. D., Boone, J. M., Wintermark, M. Augmented Reality: Advances in Diagnostic Imaging. *Multimodal Technologies and Interaction,* 2017; 1(4):29. In D3D imaging, the radiologist wears an augmented reality (AR), mixed reality (MR) or virtual reality (VR) headset and uses a joystick or gaming controller. Advantages include improved depth perception and human machine interface.

Still, there are several challenges faced with this approach. First, an area of interest (e.g. tumor) may be in close proximity to structures that are similar in composition/density. Isolating the area of interest for better examination may be difficult. Second, many soft tissues in the body are mobile and deformable, so it can be difficult to achieve the best orientation to properly compare the tumor at multiple time points. Efficiently aligning the orientation to do so may be difficult. Third, certain portions of a tumor can respond to treatment and decrease in size while other portions of a tumor demonstrate increases in size. The pattern of tumor shrinkage has important prognostic implications. Furthermore, composition and complex morphologic features including spiculations (spikes extending from the surface), irregular margins and enhancement also have important implications. Consequently, there is a need for a system that facilitates recognition of the subtle, yet important changes in size, shape and margins. Fourth, a patient with metastatic cancer has several areas of interest in different areas of the body. It is difficult and time consuming to find each of the areas of interest at every time point to determine interval change. Consequently, there is a need for a system that enables the observer to do this efficiently.

SUMMARY

All examples, aspects and features mentioned in this document can be combined in any technically possible way.

In accordance with an aspect of the invention a method comprises: generating a three-dimensional cursor that has a non-zero volume; responsive to a first input, moving the three-dimensional cursor within a three-dimensional image; responsive to a second input, selecting a volume of the three-dimensional image designated by the three-dimensional cursor; and responsive to a third input, presenting a modified version of the selected volume of the three-dimensional image. In some implementations presenting the modified version of the selected volume of the three-dimensional image comprises removing an un-selected volume of the three-dimensional image from view. In some implementations presenting the modified version of the selected volume of the three-dimensional image comprises changing transparency of presented tissues within the selected volume. In some implementations presenting the modified version of the selected volume of the three-dimensional image comprises filtering a selected tissue to remove the selected tissue from view. In some implementations presenting the three-dimensional cursor with measurement markings on at least one edge, surface or side. In some implementations presenting the modified version of the selected volume of the three-dimensional image comprises presenting inputted location indicators. In some implementations presenting the modified version of the selected volume of the three-dimensional image comprises presenting inputted annotations. Some implementations comprise changing a size dimension of the three-dimensional cursor responsive to a fourth input. Some implementations comprise changing a geometric shape of the three-dimensional cursor responsive to a fifth input. Some implementations comprise automatically generating a statistical representation of the selected volume of the three-dimensional image. In some implementations presenting the modified version of the selected volume of the three-dimensional image comprises presenting at least one tissue type with false color. In some implementations presenting the modified version of the selected volume of the three-dimensional image comprises presenting volumetric changes over time with false color. Some implementations comprise presenting multiple computed tomography images associated with the selected volume using reference lines.

Some implementations comprise presenting multiple axial computed tomography images associated with the selected volume using reference lines. Some implementations comprise presenting a maximum intensity projection (MIP) image of a positron emission tomography (PET) scan with the three-dimensional cursor overlaid thereon to indicate orientation and location of the selected volume. Some implementations comprise presenting a radiology report enhanced with information obtained using the three-dimensional cursor. Some implementations comprise automatically calculating and presenting a quantitative analysis and a qualitative analysis associated with multiple time points. Some implementations comprise presenting the modified version of the selected volume of the three-dimensional image comprises presenting inputted registration markers. Some implementations comprise automatically calculating volumetric change based on the registration markers. Some implementations comprise automatically re-orienting the selected volume of the three-dimensional image based on the registration markers. Some implementations comprise using multiple volumes selected with the three-dimensional cursor to designate a pre-operative planning pathway for guiding surgical intervention. Some implementations comprise presenting the selected volume with an augmented reality, virtual reality or mixed reality headset.

In accordance with an aspect of the invention an apparatus comprises: a computing device; and a human-machine interface comprising a three-dimensional cursor that has a non-zero volume; the human-machine interface moving the three-dimensional cursor within a three-dimensional image responsive to a first input; the human-machine interface selecting a volume of the three-dimensional image designated by the three-dimensional cursor responsive to a second input; and the human-machine interface presenting a modified version of the selected volume of the three-dimensional image responsive to a third input. In some implementations, the human-machine interface removes an un-selected volume of the three-dimensional image from view. In some implementations, the human-machine interface changes transparency of presented tissues within the selected volume. In some implementations, the human-machine interface filters a selected tissue to remove the selected tissue from view. In some implementations, the human-machine interface presents the three-dimensional cursor with measurement markings on at least one edge, surface or side. In some implementations, the human-machine interface receives and implements inputted location indicators. In some implementations, the human-machine interface receives and implements inputted annotations. In some implementations, the human-machine interface changes a size dimension of the three-dimensional cursor responsive to a fourth input. In some implementations, the human-machine interface changes a geometric shape of the three-dimensional cursor responsive to a fifth input. In some implementations, the human-machine interface automatically generates and presents a statistical representation of the selected volume of the three-dimensional image. In some implementations, the human-machine interface presents at least one tissue type with false color. In some implementations, the human-machine interface presents volumetric changes over time with false color. In some implementations, the human-machine interface presents multiple computed tomography images associated with the selected volume using reference lines. In some implementations, the human-machine interface presents multiple axial computed tomography images associated with the selected volume using reference lines. In some implementations, the human-machine interface presents a maximum intensity projection (MIP) image of a positron emission tomography (PET) scan with the three-dimensional cursor overlaid thereon to indicate orientation and location of the selected volume. In some implementations, the human-machine interface presents a radiology report enhanced with information obtained using the three-dimensional cursor. In some implementations, the human-machine interface automatically calculates and presents a quantitative analysis and a qualitative analysis associated with multiple time points. In some implementations, the human-machine interface presents inputted registration markers. In some implementations, the human-machine interface automatically calculates volumetric change after appropriate registration using the registration markers. In some implementations, the human-machine interface automatically re-orients the selected volume of the three-dimensional image based on the registration markers. In some implementations, the human-machine interface presents multiple volumes selected with the three-dimensional cursor to designate a pre-operative planning pathway for guiding surgical intervention. In some implementations, the human-machine interface presents the selected volume with an augmented reality, virtual reality or mixed reality headset.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1A:
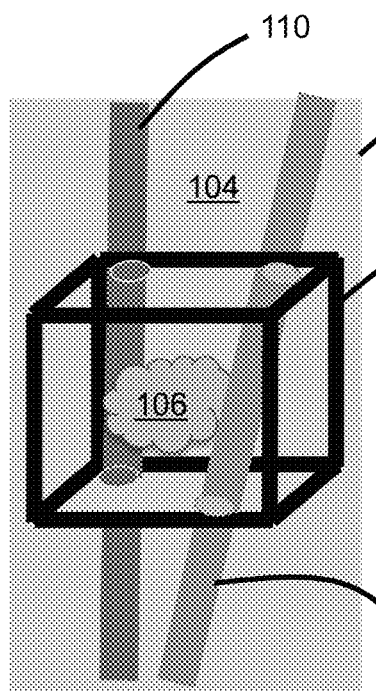
FIG. 1A illustrates a 3D cursor selecting a volume of interest from a three-dimensional medical image.

FIG. 1A illustrates a 3D (three-dimensional) cursor 100 overlaid on a three-dimensional medical image 102. In the illustrated example, the 3D cursor 100 defines a cubic volume of interest. The medical image 102 could include any portion of a body, or an entire body, for example and without limitation. For purposes of explanation the medical image 102 includes different types of tissue. More specifically, the image includes a background material 104, such as fat, a lobulated mass 106, a tubular-shaped vein 108, and an artery 110. The 3D cursor 100 can be moved relative to the image, e.g. in three dimensions, such as by manipulating an IO device such as a 3D mouse, for example and without limitation. A button click or other input designates (selects) the portion of the image that is located inside the three-dimensional volume of the 3D cursor 100. Distinguishing between a 3D image portion selected by a 3D cursor and other unselected image portions is described in US 2016/0026266 and U.S. Pat. No. 8,384,771, both of which are incorporated by reference.

Figure 1B:
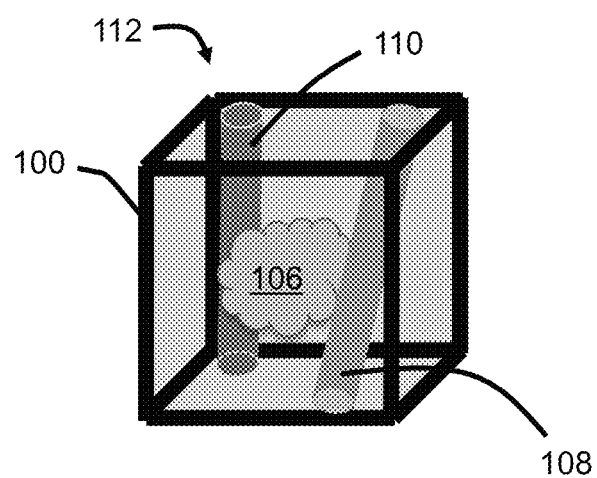
FIG. 1B illustrates the volume of interest selected with the 3D cursor; unselected portions have been removed from view.

FIG. 1B illustrates the selected image portion of FIG. 1A. More particularly, unselected portions of the image located outside of an image portion 112 selected with the 3D cursor 100 have been filtered-out or otherwise completely removed from view. Consequently, the removed portions of the image do not obstruct or hinder the view of the selected image portion. Moreover, the selected image portion 112 can be manipulated and viewed as a separate and distinct image from the larger medical image 102 from which it was selected.

Figure 1C:
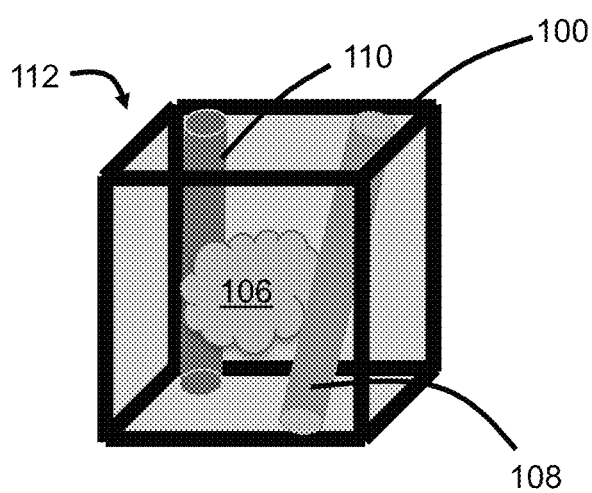
FIG. 1C illustrates modification of the transparency of the selected volume of interest.

FIG. 1C illustrates modification of the transparency of the selected image portion 112. More specifically, transparency may be decreased and/or increased such that tissues and other features can be better observed, e.g. such that overlapping tissues and features are visible. For example, tissues and features located proximate to the back of the selected image portion such as lobulated mass 106 can be seen through overlapping tissues and features located proximate to the front of the selected image portion such as vein 108, when transparency is sufficiently increased. The transparency may be manipulated with the IO device to achieve various levels of transparency. Further, different levels of transparency may be applied to different portions of the selected image portion.

Figure 1D:
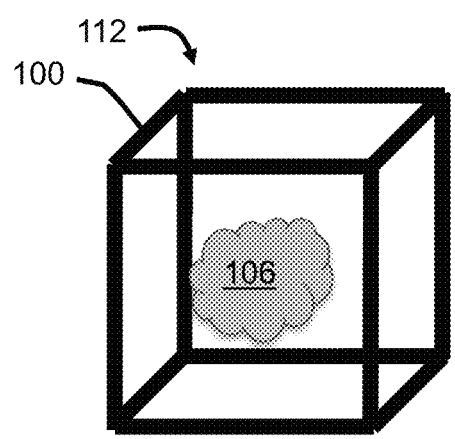
FIG. 1D illustrates filtering of selected areas of the selected volume of interest.

FIG. 1D illustrates filtering of selected areas or tissues of the selected image portion 112 to remove those areas or tissues from view. In the illustrated example the background material 104, vein 108, and an artery 110 have been removed from view, leaving only the lobulated mass 106. The tissues to be filtered (removed from view) may be selected based on geometric shape, color, brightness, density, and any other of a variety of available image data, either alone or in combination. Moreover, a designated volume defined by a geometric shape may be removed, e.g. a geometric shape that traverses tissue boundaries.

Transparency modification and tissue filtering facilitate presentation of certain tissue types of concern, both within the cursor and outside of the cursor. Currently, the medical professional must see through any tissue within the cursor but external to the tissue type of concern from the viewing point of the medical professional, thus degrading the visibility of the tissue of concern. The illustrated improvements enable the medical professional to change the transparency of any tissue within the cursor-defined volume but external to the tissue type of concern. Alternatively, tissue types not of concern are subtracted from the volume contained within the interactive 3D cursor, leaving only the tissue of concern in the presented image. Multiple interactive 3D cursors in combination can be used to obtain varying patterns of tissue subtraction. This helps to overcome the limitations of degraded visibility due to tissue within the cursor but external to the tissue type of concern from the viewing point of the medical professional.

Figure 2:
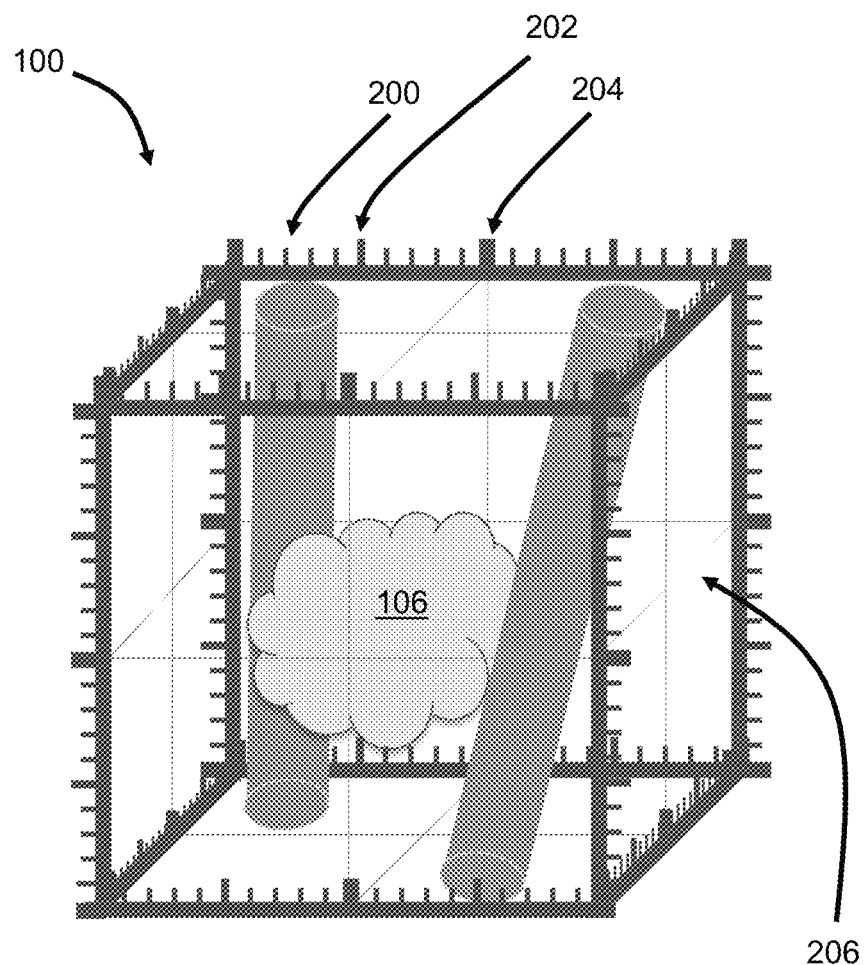
FIG. 2 illustrates a variant of the 3D cursor of FIG. 1A with measurement markings on edges and sides.

FIG. 2 illustrates an implementation of the 3D cursor 100 with dimensional measurement markings. Dimensional measurement markings may be available as a feature that can be turned ON and OFF. In the illustrated example, the 3D cursor is a 2 cm by 2 cm by 2 cm cube. The dimensional measurement markings include tick marks 200, 202, and 204 that respectively designate 1 mm, 5 mm, and 1 cm increments along the edges of the cube (and thus representing three dimensions). Tick marks that represent different magnitudes may be uniquely represented to facilitate visual size determination of the lobulated mass 106 that represents the lesion of interest. 1 cm markings 206 are presented in each of two dimensions on each side of the cube.

The dimensional measurement markings can help serve as a reference for radiologist's activities to include visual assessment, orientation, comparisons with prior scans or measurements. Advantages may include mitigating the current lack of metrics are available to the medical professional to understand the size of the cursor and/or of the tissue elements contained within the cursor. This implementation places measurement metrics on each edge and side of the cursor to help enable the medical professional to rapidly understand the size of the subtended volume within the cursor. In the case where the cursor encapsulates a volume of concern such as a tumor, the three-dimensional size could be recorded in the medical professional report. This can help the visual assessment of each portion of the tumor to aid in the assessment of small changes in size of findings including lobulations of a mass's margin and spiculations.

Figure 3:
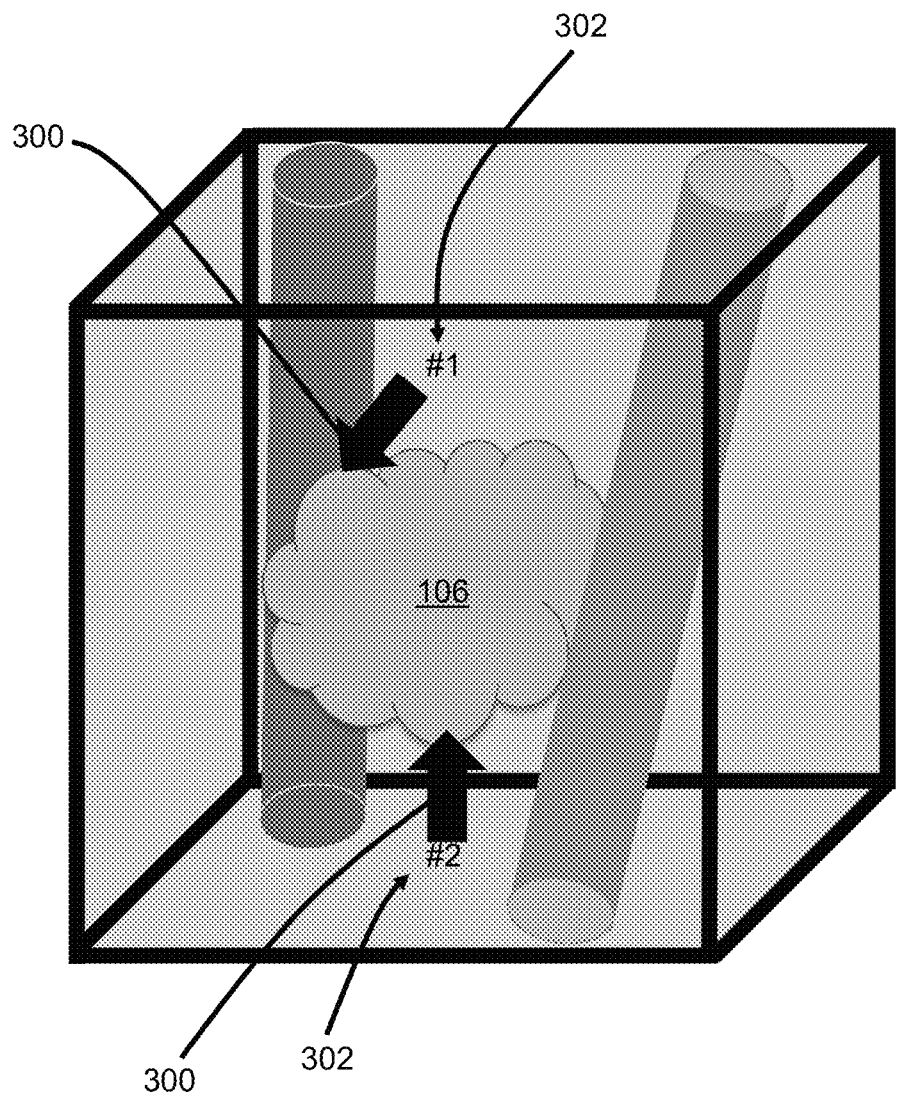
FIG. 3 illustrates location indicators and annotations positioned relative to the portion of the image within the selected volume of interest.

Referring to FIG. 3, location indicators 300 and annotations 302 may be placed by the radiologist or by automated techniques to highlight locations or regions of concern within the interactive 3D cursor. The location indicators may specify a point or region within the volume of the 3D cursor. Annotations can be added manually by the radiologist or by automated techniques to describe areas that are of concern, e.g., growing, spiculation, irregular margin, indistinct margin, etc. If spiculations are on the surface of a tumor, this could be an indicator of potential malignancy. The location indicators, such as, but not limited to, arrow(s) pointing to key regions of interest within/outside the 3D cursor helps to overcome the limitation of the inability to mark key points within the cursor. This feature will be useful in discussions between medical professions regarding a patient's condition. It will also be useful in communicating imaging findings between a medical professional and a patient.

Figure 4A:
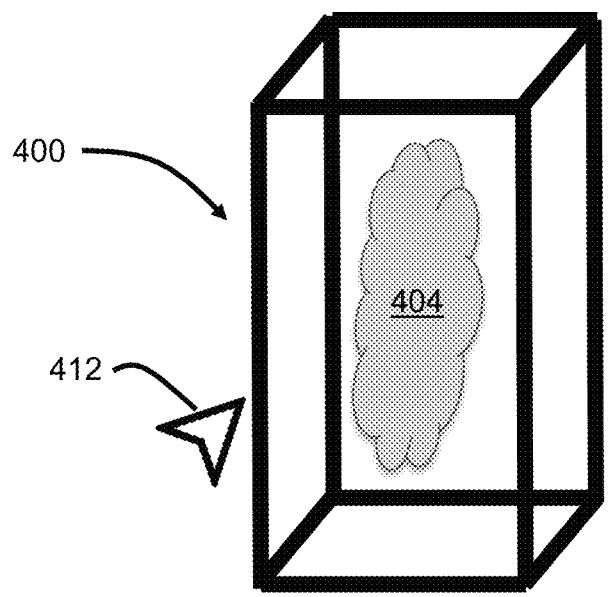
FIGS. 4A, 4B, and 4C illustrate three different examples of geometric shapes of the 3D cursor of FIG. 1A.
Figure 4B:
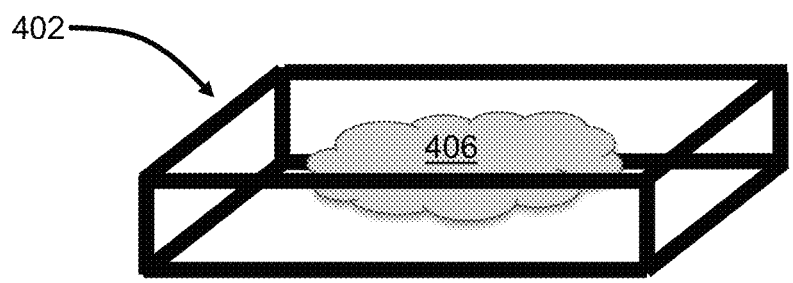
Figure 4C:
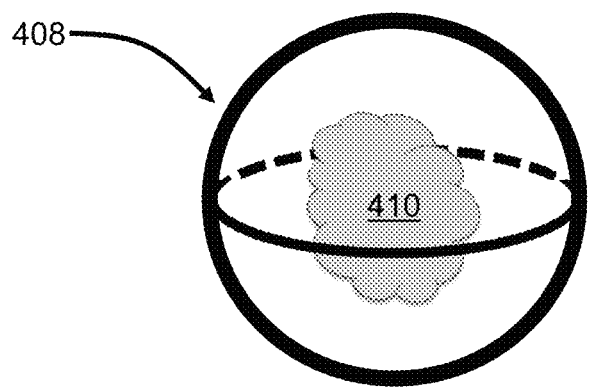

Referring to FIGS. 4A, 4B, and 4C, the 3D cursor may be implemented in a wide variety of different shapes. Examples include but are not limited to cube, cuboid, cylinder, sphere, ellipsoid, cone and tetrahedron. The shapes are not necessarily regular, and the lengths of edges may be resized, e.g. overall geometric shape scaling or changing individual edges, sides, or surfaces. For example, FIGS. 4A and 4B illustrate cuboid 3D cursors 400, 402 for which edge length has been set or selected based on the dimensions and orientation of the respective feature of interest 404, 406. FIG. 4C illustrates a spherical 3D cursor 408 for which the diameter may be set or selected based on the dimensions of the feature of interest 410. In addition to dimensional changes, cursor geometric shape may be changed.

The ability to change the size, shape, and individual dimensions of the 3D cursor enables the cursor to be customized based on the particular volume of interest to the medical professional. A fixed-shape, fixed-size cursor might be too large or too small, e.g. so as to include a significant amount of tissue not of interest. For example, in examining the lungs, placement of a cube-shaped cursor could cause ribs to be included in the image. Changing the shape of the 3D cursor would help to overcome this limitation. Customization could be accomplished by wide variety of techniques, possibly including but not limited to selecting an edge, side or vertex of the original 3D cursor with a second type of cursor 412, and then "clicking and dragging" the selected edge, side, or vertex in the desired direction to expand or reduce the volume of the original 3D cursor. The interface may also enable selection and change between multiple 3D geometric shapes, e.g. changing from cuboid to spherical. Scrolling on the conventional slices while simultaneously drawing shapes can also be performed to generate the prescribed 3D cursor volume. The interactive 3D cursor thus provides an efficient interface for tissue subtraction to provide enhanced visualization of the tumor.

Figure 5:
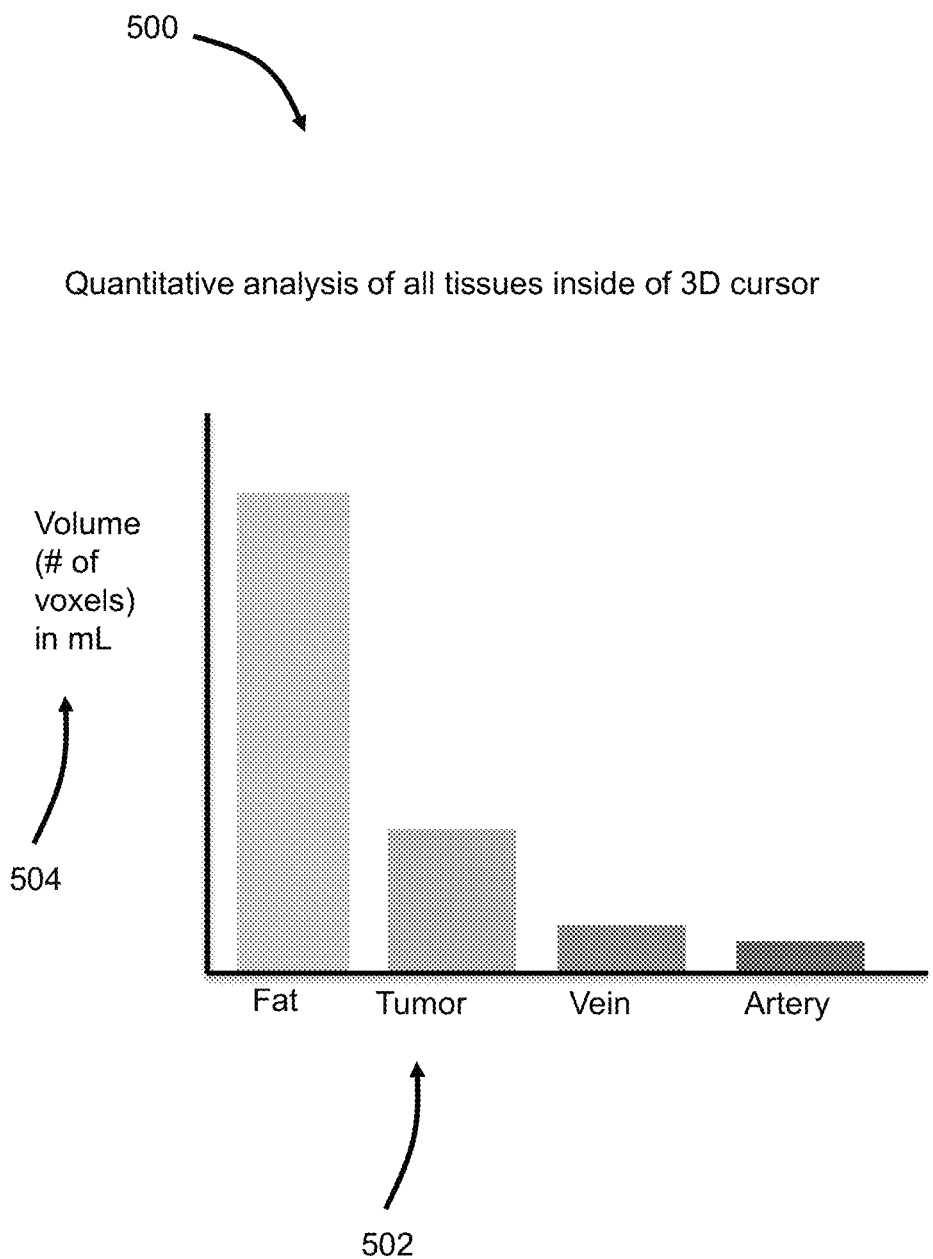
FIG. 5 illustrates presentation of a quantitative analysis of tissues inside of the volume of interest selected with the 3D cursor of FIG. 1A.

FIG. 5 illustrates presentation of a quantitative analysis 500 of all tissues inside a volume selected with the 3D cursor. The illustrated example includes a bar graph but it is to be understood that any of a wide variety of charts, graphs, and other techniques for presentation of data might be implemented. Quantitative analysis can help the radiologist understand how a feature of interest such as tumor 502 (e.g., the lobulated mass 106, FIG. 1B) is changing in volume 504 over multiple time points. The interface may include a statistical representation of the tissue types, possibly including but not limited to a histogram bar chart to depict the volume (e.g., number of voxels per unit volume) of the different types of tissue within the cursor, distinct markings for different types of tissue such as, but not limited to, color coding the bars of the histogram bar chart.

Figure 6:
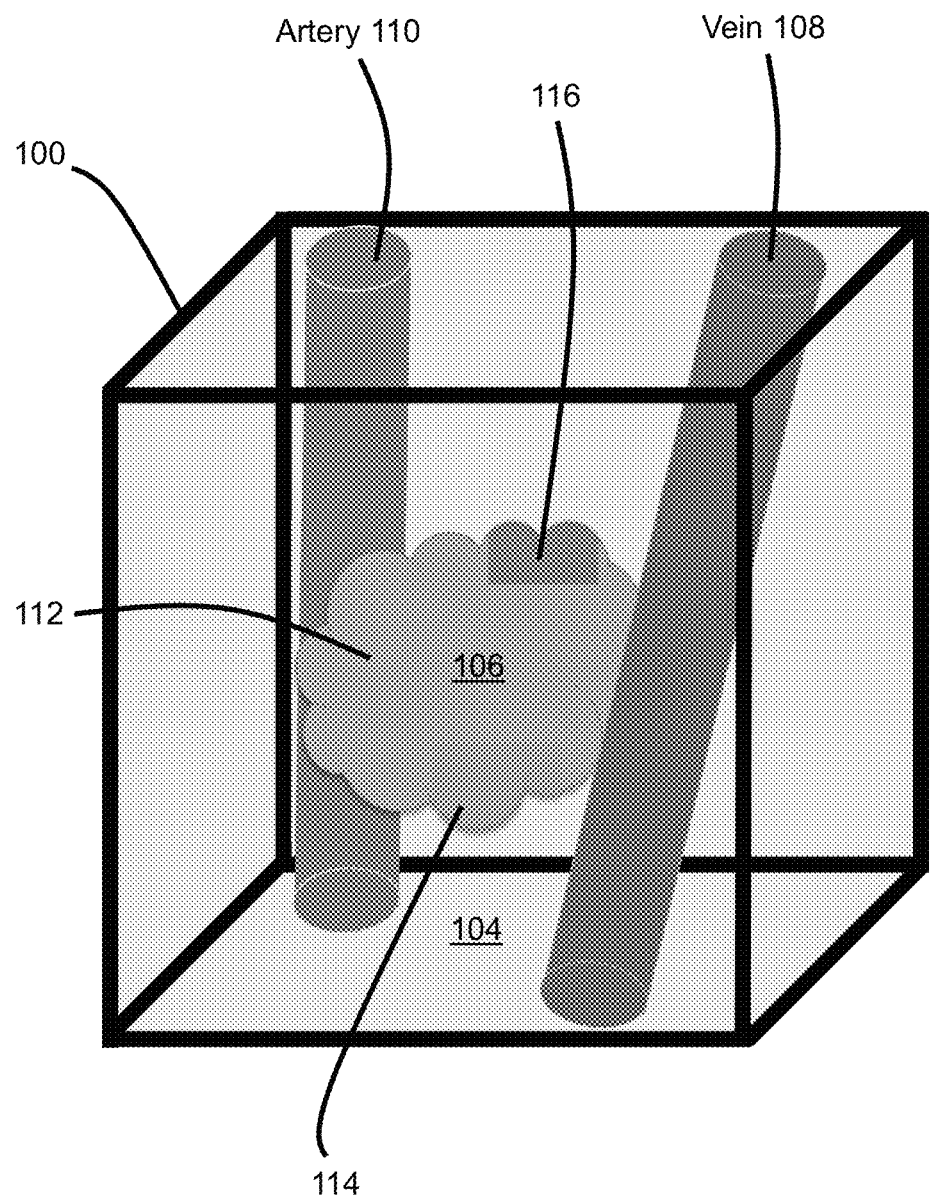
FIG. 6 illustrates use of false color and transparency changes to enhance viewing of the selected volume of interest.

FIG. 6 illustrates an implementation of the interactive 3D cursor 100 with false color and transparency to enhance viewing. False color and transparency may be dynamically adjusted and turned ON and OFF. Different false colors may be applied to different tissue types within the volume of the 3D cursor. The colors could be selected to correspond to the colors used in the statistical representation (FIG. 5). Alternatively, a respective unique false color could be selected for each different tissue type, or tissue types of particular interest or concern, and/or additional features of concern, e.g., irregular margin, indistinct margin, spiculation, etc. In the illustrated example, the background material 104 (fat) is depicted in light gray, the artery 110 is depicted in red, the vein 108 is depicted in blue, and the lobulated mass 106 is multicolored. Different colors may be selected or used to indicate stability of the lobulated mass 106 over time. For example, green may be used to indicate a stable volume 112 while orange is used to denote a slow growth volume 114, thereby providing a visual warning indicator. Red may be used to indicate high rate of growth or concerning margin volume 116. The extent of the volume of the lobulated mass can be determined automatically, e.g. based on density. Moreover, changes in volume of sub-regions of the lobulated mass may also be automatically determined, and color coding may be automatically implemented. This can help the radiologist understand how the mass is changing in volume over multiple time points.

Figure 7:
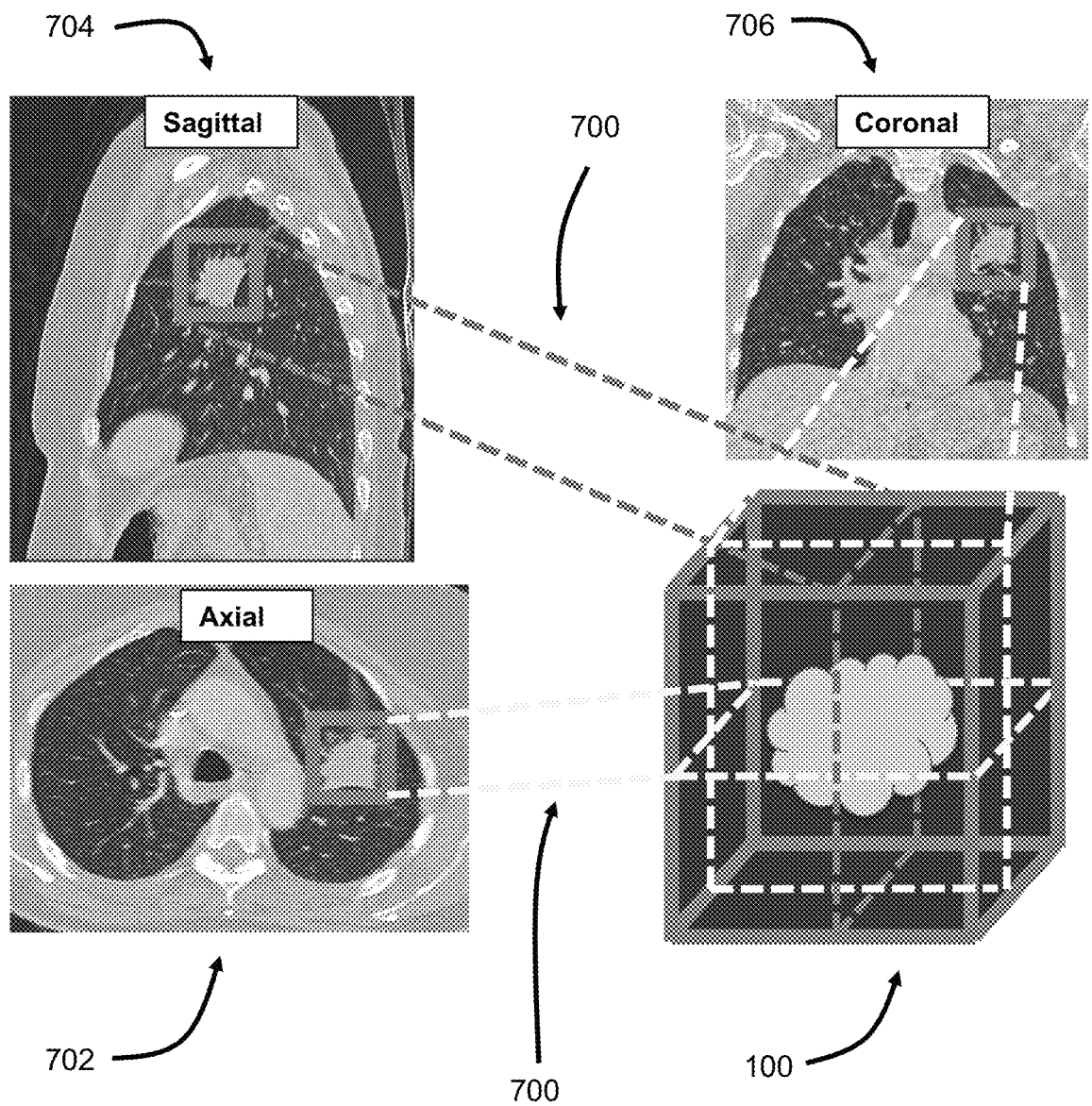
FIG. 7 illustrates association of multiple computed tomography (CT) images of the chest in lung windows with the interactive 3D cursor using reference lines.

FIG. 7 illustrates association of multiple computed tomography (CT) images of the chest in lung windows with the interactive 3D cursor 100 using reference lines 700. The illustrated example includes an axial image 702, a sagittal image 704, and a coronal image 706 of the chest in lung windows. An advantage is enhanced ability to cross reference the 3D cursor to the original 2D slices 702, 704, 706 from which total 3D volume was obtained. Medical professionals have experience and familiarity with 2D slices and may feel more confident in their findings given the capability to switch back and forth between the 2D and 3D volumetric approaches. A small display adjacent to the interactive 3D cursor could indicate which 2D slices contain tissue within in the interactive 3D cursor. Then the medical professional could direct the system to automatically select those slices which have tissue within the cursor and display them on a nearby 2D display unit. A corresponding visible boundary of the 3D cursor (e.g., red) projected on each of the slices may be presented.

Figure 8:
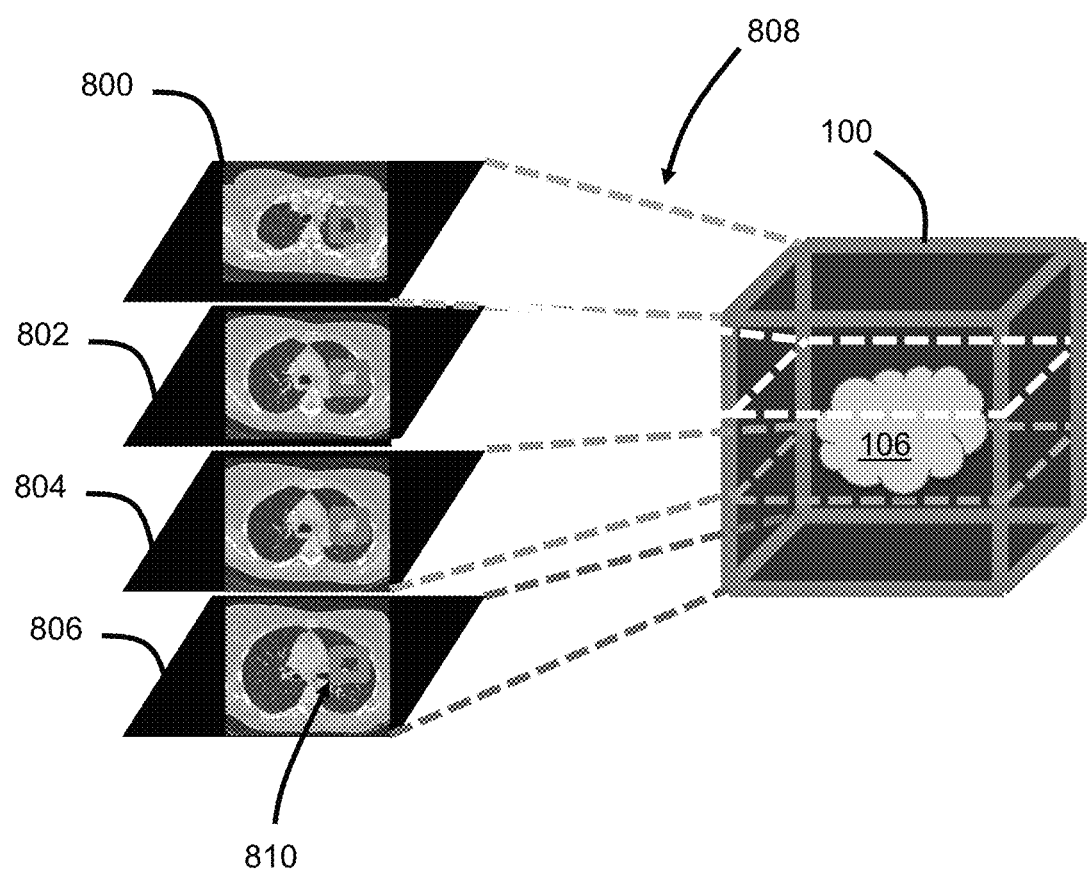
FIG. 8 illustrates association of multiple axial computed tomography (CT) slices of the chest in lung windows with the interactive 3D cursor using reference lines.

FIG. 8 illustrates association of multiple axial computed tomography (CT) slices 800, 802, 804, 806 of the chest in lung windows with the interactive 3D cursor 100 using reference lines 808. The multiple axial computed tomography (CT) slices of the chest in lung windows show the location of the 3D cursor, i.e. the slice area that includes a cross-section of the 3D cursor, which in the illustrated example has selected a left upper lobe mass. Boundaries 810 of the 3D cursor in the slices are depicted in a color, e.g. red. Within the 3D cursor the lung cancer mass 106 is depicted in gray, surrounded by black that indicates non-cancerous lung tissue. This implementation helps the medical professional to rapidly visualize where the interactive 3D cursor is located relative to the slice images and the body. It also enables the medical professional to visualize the entire volumetric data with the interactive 3D cursor accurately positioned within the volume. Transparency of tissue within the 3D volume could be changed so that the interactive 3D cursor would stand out. This would help avoid left-right orientation mistakes that might occur during treatment. Multiple interactive 3D cursors which could be of differing sizes and/or shapes could be created and displayed.

Figure 9:
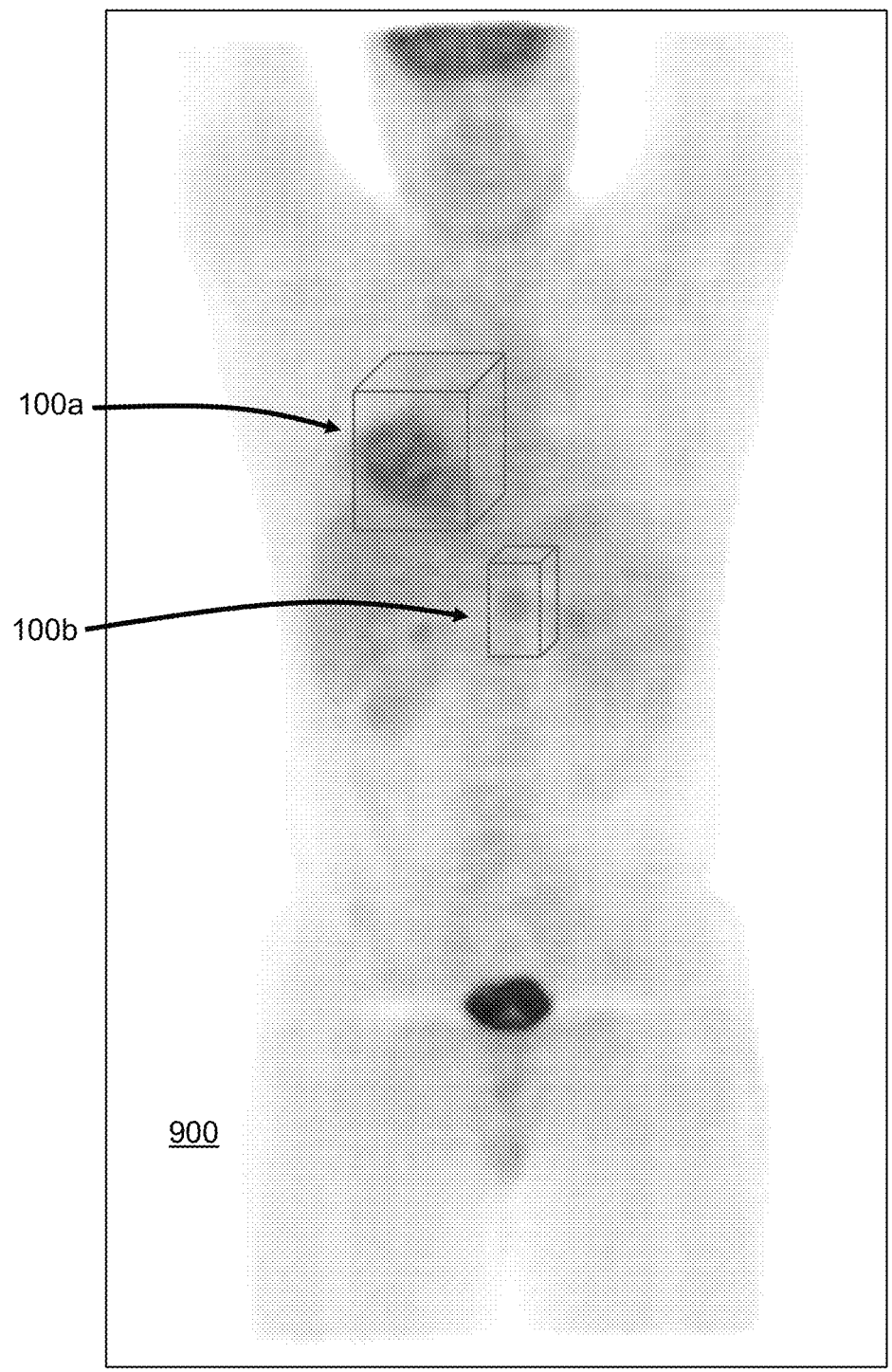
FIG. 9 illustrates a maximum intensity projection (MIP) image of a fludeoxyglucose (18F) positron emission tomography (PET) scan in which two varying sized interactive 3D cursors are overlaid to indicate 3D cursor shape, size, orientation, and location when respective volumes of interest were selected.

FIG. 9 illustrates overlay of 3D cursors 100a, 100b on a maximum intensity projection (MIP) image 900 of a fludeoxyglucose (18F) positron emission tomography (PET) scan. Two different-sized interactive 3D cursors are used to highlight two separate areas of concern, including 3D cursor 100a for a right lung mass and cursor 100b for a vertebral body metastasis. This helps to automatically transfer data (e.g., picture of tissue within the cursor and statistical representations) from the viewing modality to the report of findings. Selection of key data through human machine interface such as, but limited to, a screen capture can be automatically transferred to the report of findings. This would provide quantitative results within the report together with qualitative impressions of the medical professional.

Figure 10:
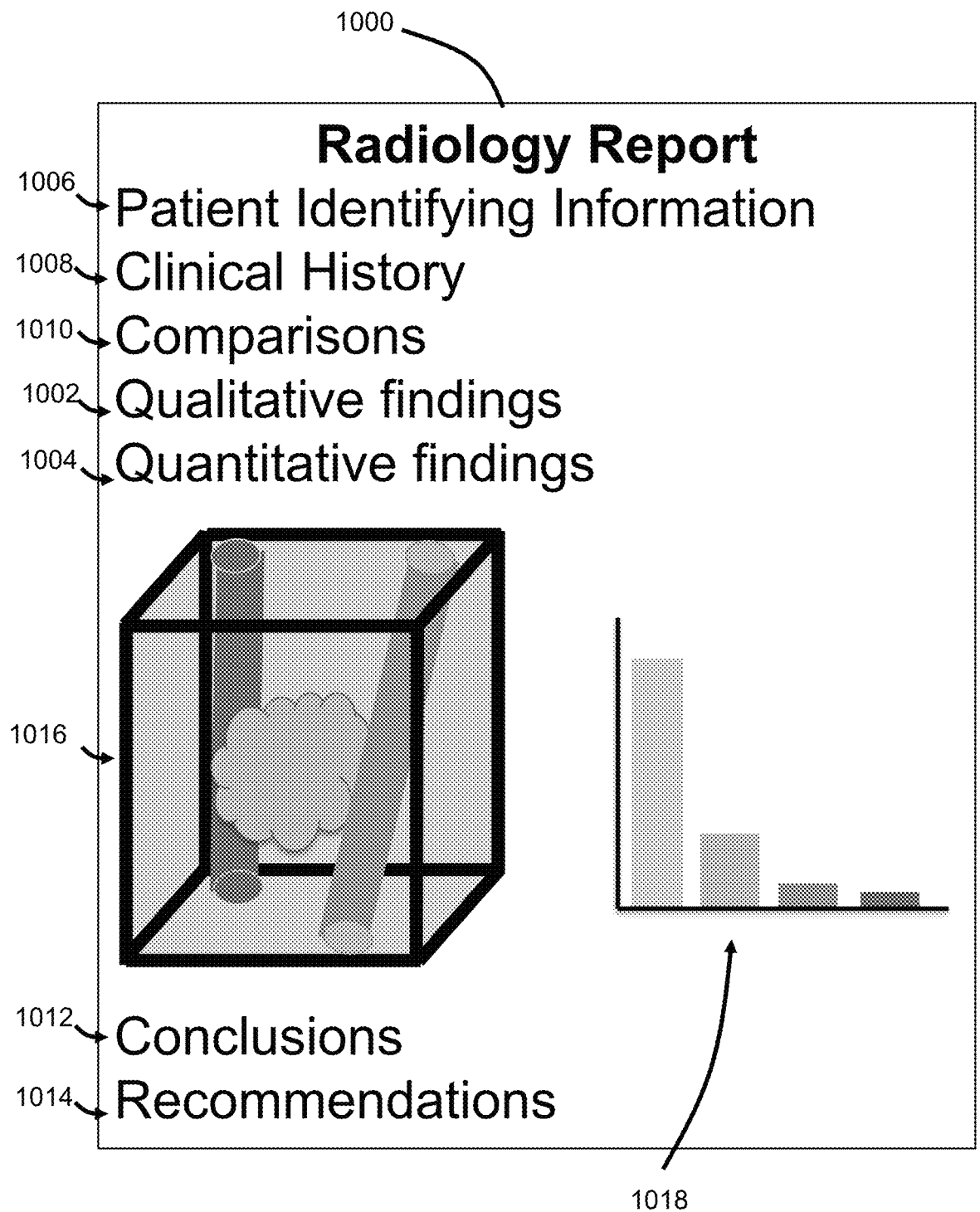
FIG. 10 illustrates a radiology report enhanced with information obtained using the interactive 3D cursor and including quantitative and qualitative analysis.

FIG. 10 illustrates a radiology report 1000 enhanced with information obtained from the interactive 3D cursor. Qualitative findings 1002 and quantitative findings 1004 may be included along with patient identifying information 1006, clinical history 1008, comparisons 1010, conclusions 1012, and recommendations 1014. Also included are a selected volume image 1016 and statistical graphic 1018. This helps to quantitatively track changes in volumes of concern (e.g., tumors) over time.

Figure 11:
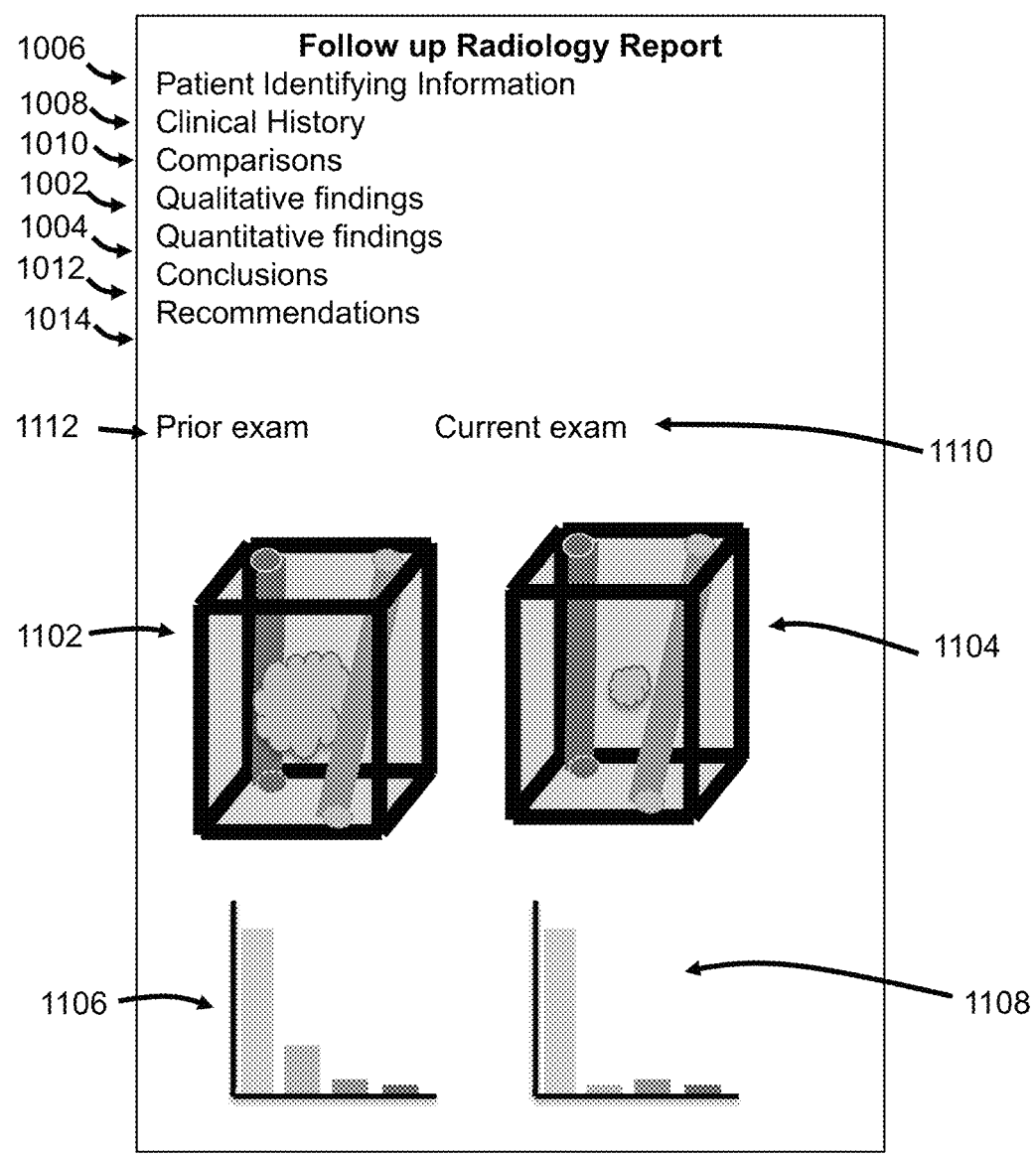
FIG. 11 illustrates a radiology report enhanced with information obtained using the interactive 3D cursor, and including added quantitative and qualitative analysis at multiple time points.

FIG. 11 illustrates a radiology report 1100 enhanced with information obtained from the interactive 3D cursor at multiple time points. Qualitative findings 1002 and quantitative findings 1004 may be included along with patient identifying information 1006, clinical history 1008, comparisons 1010, conclusions 1012, and recommendations 1014. Also included are selected volume images 1102, 1104 from different time points and respective statistical graphics 1106, 1108 from those time points. Follow up reports can include current and prior exams 1110, 1112 with quantitative analysis and qualitative analysis on how the lesion has changed over time. This may facilitate selection of a lesion (e.g., tumor) at multiple time points using an interactive 3D cursor; qualitative assessment of the lesion at multiple time points; and, quantitative assessment of the lesion at multiple time points. This would enable the medical professional to better assess how a particular lesion is changing over time. A report of current findings as outlined in the previous implementation could be placed in a report together with the data obtained from an earlier examination. This would enable tracking over time the progress of treatment or that of changes in tissues of interest/concern.

Figure 12A:
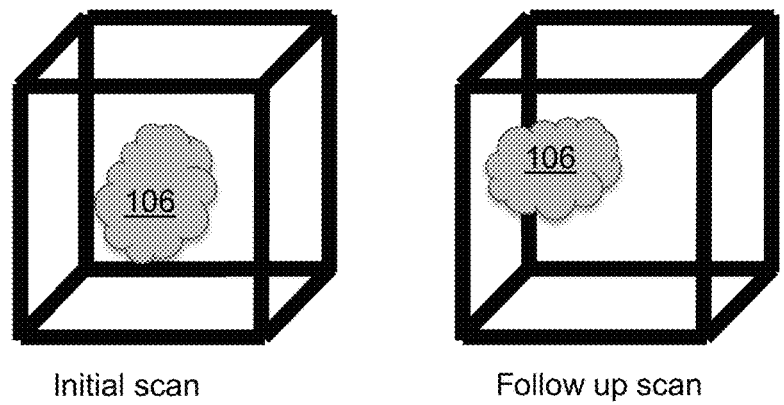
FIGS. 12A, 12B and 12C illustrate a technique for correction for mis-registration at multiple time points using three or more markers.
Figure 12B:
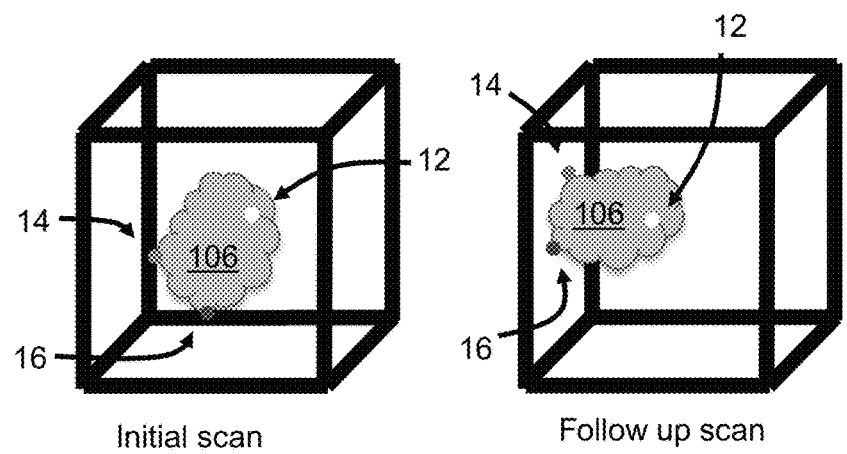
Figure 12C:
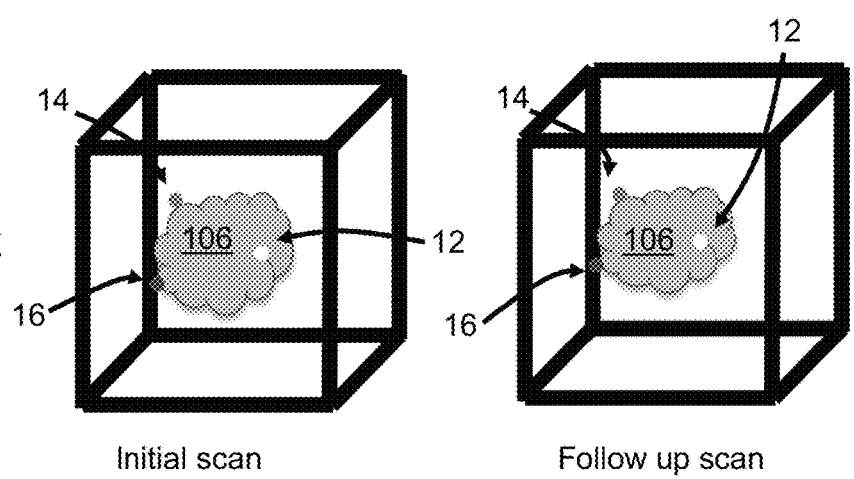

FIGS. 12A, 12B, and 12C illustrate a registration technique by which mis-registration can be corrected at multiple time points through the use of three or more markers 12, 14, 16. Initially, the mass 106 within each 3D cursor 100 image is noted using different locations within the interactive 3D cursor and different orientations. Next, the user marks similar locations on each image of the mass with registration markers. In the illustrated example, a yellow marker 12, a red marker 14, and a blue marker 16 correspond to the same respective parts of the mass on each scan. Finally, tissues within the interactive 3D cursor are aligned in accordance with markers. Many soft tissues within the body can change in orientation from one scan to the next due to patient movement. Corresponding mis-registration can limit the ability to properly track how a lesion changes over time. This technique provides a method to correct for such mis-registration. Three or more recognizable spots of the lesion (e.g., tumor) can be marked with a false color, arrow, or other registration mark. Then, these locations can be automatically aligned with one another. Shadows can be added to help bring out depth perception. Proper alignment will accurately align the shadows. This enhances visual assessment for how a lesion is changing over time to include changes in tumor composition, size and morphology.

Figure 13:
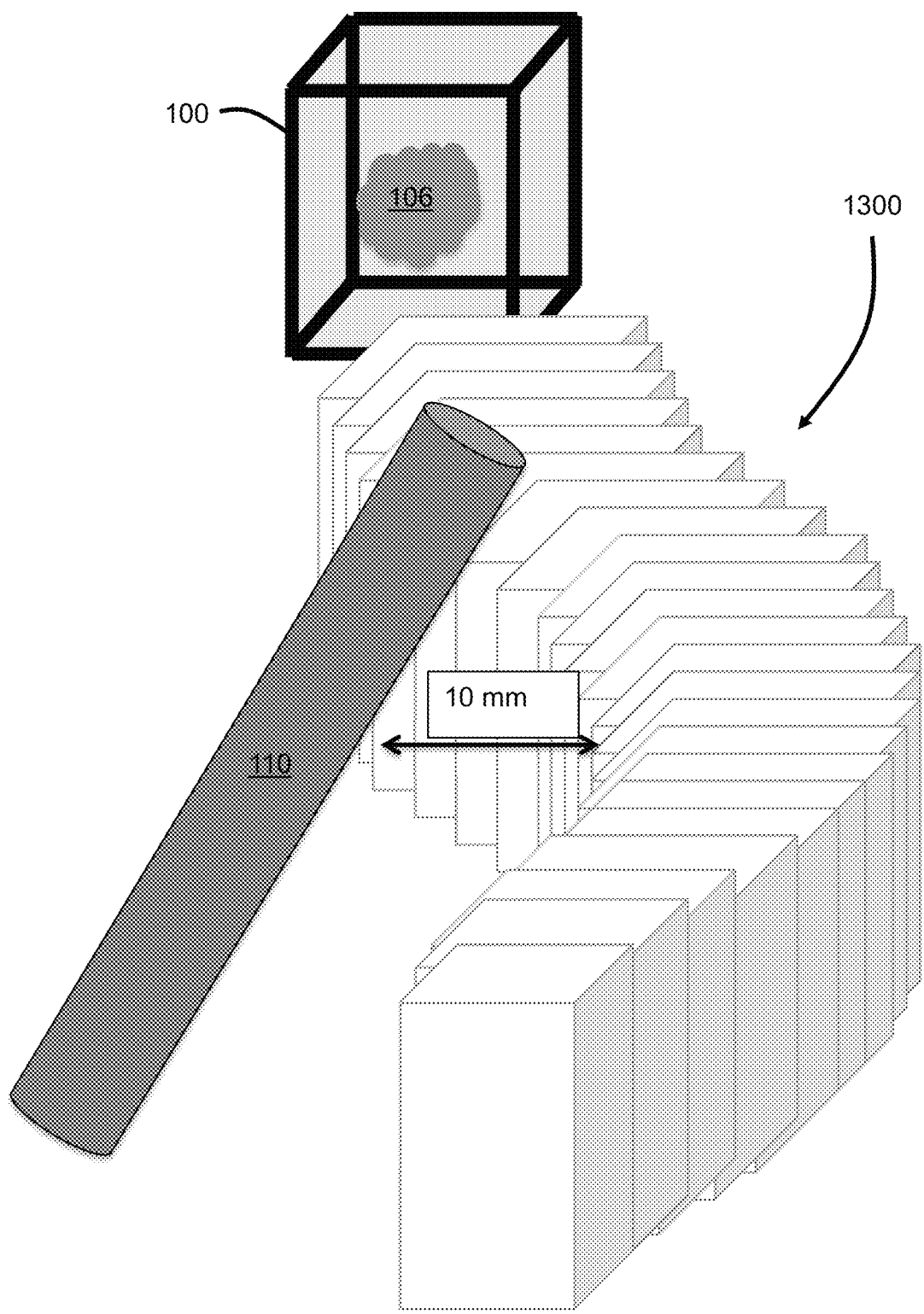
FIG. 13 illustrates use of multiple interactive 3D cursors to select volumes of interest to designate a safe pre-operative planning pathway for guiding surgical intervention.

FIG. 13 illustrates use of multiple image volumes selected with the 3D cursor to designate a safe pre-operative planning pathway to guide surgical intervention. In the illustrated example, multiple green interactive 3D cursors 1300 mark a surgeon-selected dissection pathway that is deemed safe in the pre-operative setting. The interactive 3D cursor 100 containing the cancerous lesion 106 is shown at a distal end of the planned surgical path represented by abutting or overlapping volumes selected with the 3D cursors 1300. The selected path that the surgeon will excise avoids the artery 110 with a minimum clearance of 10 mm. This provides the advantage of 3D depiction of possible surgical cuts. The path could include, but is not limited to, one or more of the following properties: a serpentine shape; measurements could subsequently be made to measure absolute distance between a point on the planned path to some region of concern (e.g., artery); the path could also be projected on a head mounted display at different intervals during the course of the operation. This feature would facilitate surgical planning as well as a potential to improve accuracy of the surgery.

Figure 14:
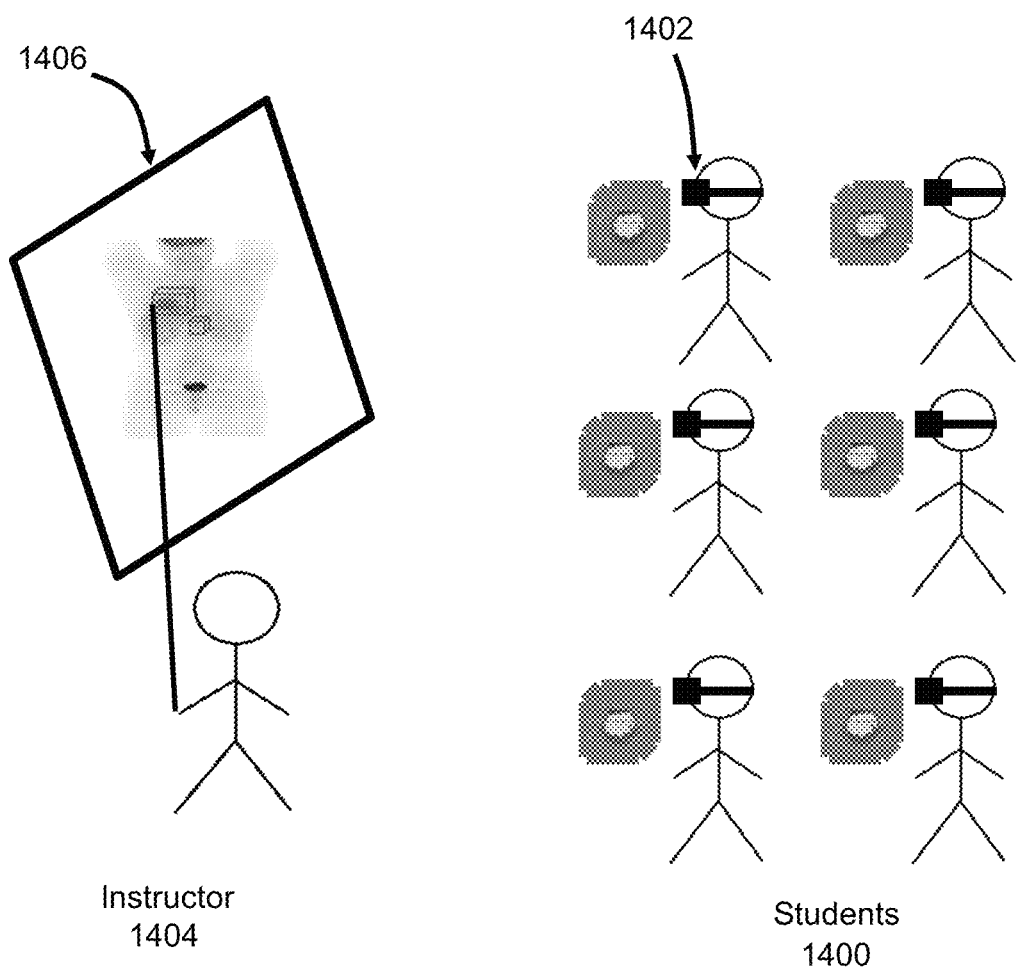
FIG. 14 illustrates use of the interactive 3D cursor in an educational setting.

FIG. 14 illustrates use of the interactive 3D cursor in an educational setting. Students 1400 are depicted wearing AR (augmented reality) headsets 1402 and an instructor 1404 is pointing to an abnormality on the board 1406. This facilitates presentation of medical information (e.g., anatomy) in a classroom environment. The interactive 3D cursor could be placed around the organ of interest and other parts of the body could be eliminated. Items from implementations discussed above such as metrics and arrows could be used. The students would be provided 3D head displays and joined into a display system so that they could see the tissue within the interactive 3D cursor. This would eliminate any confusion on the part of the students as to what specific detail in the imagery was being discussed.

Figure 15:
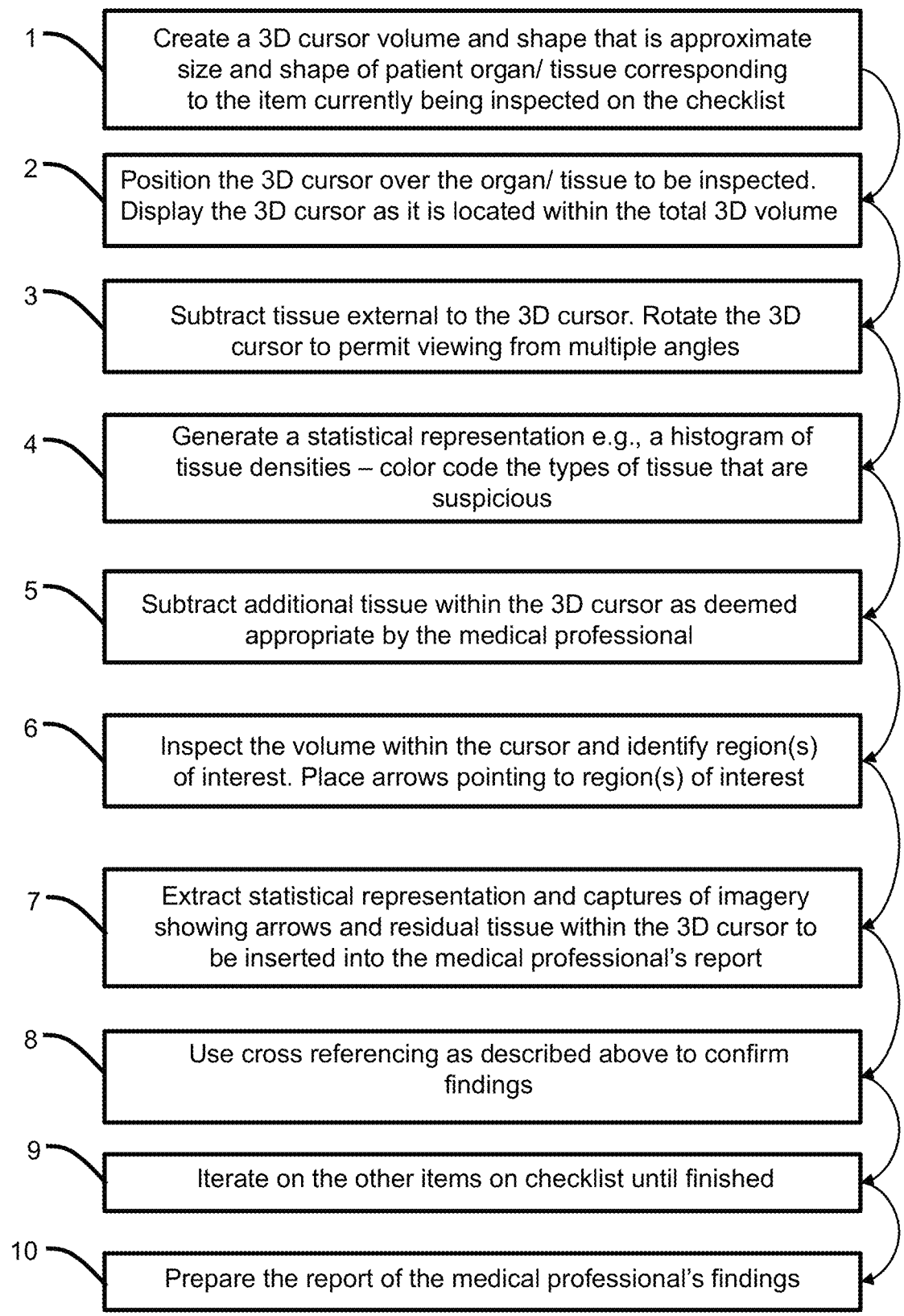
FIG. 15 illustrates process steps on a radiologist's review of a patient's image with integration of the interactive 3D cursor.

FIG. 15 illustrates process steps on a radiologist's review of a patient's image with integration of the interactive 3D cursor into his/her practice. Step 1 is to create an interactive 3D cursor volume and shape that approximates the size and shape of patient organ/tissue corresponding to the item currently being inspected on the checklist. Step 2 is to position the interactive 3D cursor over the organ/tissue to be inspected. The interactive 3D cursor as it is located within the total 3D image volume may be presented on a display. Step 3 is to subtract from view all tissue external to the interactive 3D cursor. The interactive 3D cursor may be rotated to permit viewing from multiple angles. If interactive cursors are used at multiple time points to track how a particular lesion (e.g., tumor) changes over time, the 3D cursors can be rotated in synchrony with on another. Step 4 is to generate a statistical representation e.g., a histogram of tissue densities—color coded with the types of tissue that are suspicious. Step 5 is to subtract from view additional tissue within the interactive 3D cursor as deemed appropriate by the medical professional. Step 6 is to inspect the volume within the cursor and identify region(s) of interest and place indicators, annotations, and registration markers relative to region(s) of interest. Step 7 is to extract a statistical representation and capture imagery showing indicators, annotations, and registration markers and residual tissue within the interactive 3D cursor to be inserted into the medical professional's report. Step 8 is to use cross-referencing as described the above to confirm findings. Step 9 is to iterate on the other items on the checklist until finished. Step 10 is to prepare the report of the medical professional's findings. This procedure provides an opportunity to enhance medical image review process by medical professionals.

Figure 16:
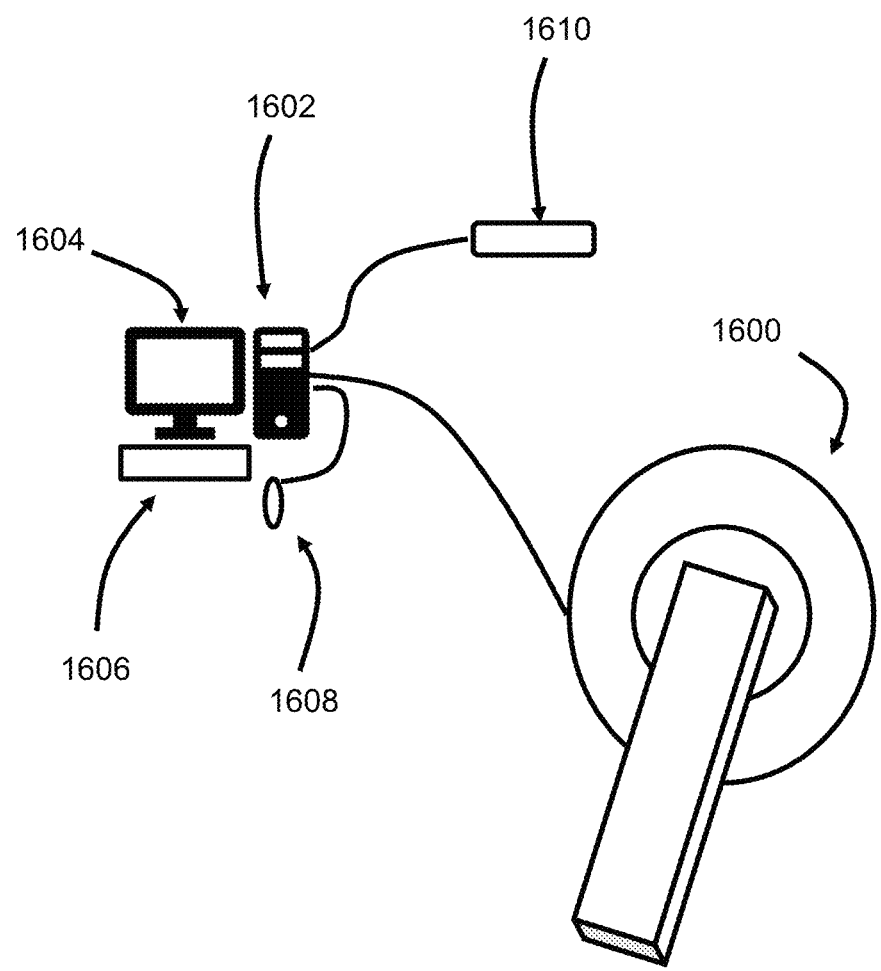
FIG. 16 illustrates a system for use of the interactive 3D cursor.

FIG. 16 illustrates a system for use of the interactive 3D cursor. A medical imaging device 1600 is connected to a computer workstation 1602. A wide variety of medical imaging devices and computer workstations could be used. Images are captured by the medical imaging device and sent to the computer workstation. The computer workstation includes non-volatile storage, computer-readable memory, processors, and a variety of other resources including but not limited to IO devices that provide a human-machine interface. In the illustrated example, the IO devices include a monitor 1604, keyboard 1606, 3D mouse 1608, and VR headset 1610. The IO devices are used to prompt a software program that runs on the computer workstation to perform the various process steps and implement the various features that have already been described above.

There are multiple potential advantages of the interactive 3D cursor. For example, there is reduction in time spent for classification of multiple lesions. The radiologist doesn't have to sort through many prior imaging studies to find the lesion and the interactive 3D cursor will save time. There is reduction in error when tracking multiple lesions, i.e. reducing the likelihood of mistakes when identifying different specific lesions that are nearby one another when comparing multiple scans. One possibility is to analyze the images obtained using the 3D cursor and using multiple uniquely tagged (e.g. numbered) cursors for any suspicious regions. The medical profession could then switch to slices for confirmation.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
generating a three-dimensional cursor that has a non-zero volume;
selecting a three-dimensional image volume designated by the three-dimensional cursor, wherein the three-dimensional cursor encloses the selected volume; and
displaying the three-dimensional cursor including measurement markings that serve as constituent unit measurement indicators of a size of an element within the selected volume.

2. The method claim 1, further comprising presenting a modified version of the selected volume.

3. The method of claim 2 wherein presenting the modified version of the selected volume comprises removing an un-selected volume of the three-dimensional image volume from view by making the un-selected volume transparent.

4. The method of claim 2 wherein presenting the modified version of the selected volume comprises subtracting an un-selected volume of the three-dimensional image volume from view by eliminating voxels comprising the un-selected volume.

5. The method of claim 2 wherein presenting the modified version of the selected volume comprises presenting inputted location indicators on the at least one edge, surface or side of the three-dimensional cursor.

6. The method of claim 2 wherein presenting the modified version of the selected volume of the three-dimensional image comprises presenting inputted annotations on the at least one edge, surface or side of the three-dimensional cursor.

7. The method of claim 1 further comprising changing the volume inside of the three-dimensional cursor by moving the three-dimensional cursor to a different position within the three-dimensional image.

8. The method of claim 1 further comprising changing the volume inside of the three-dimensional cursor by changing the three-dimensional cursor's shape.

9. The method of claim 1 further comprising presenting a statistical representation of the selected volume of the three-dimensional image to a user.

10. The method of claim 2 wherein presenting the modified version of the selected volume comprises presenting a subset of voxels with false color based on the subset of voxels' composition.

11. The method of claim 1 further comprising:
wherein said volume of said three-dimensional image is from a first imaging examination;
using the three-dimensional cursor for an additional imaging examination; and
wherein presenting the modified version of the selected volume comprises presenting volumetric changes of a structure within the three-dimensional cursor from said first imaging examination to said additional imaging examination with false color.

12. The method of claim 11 further comprising performing and presenting a quantitative analysis of said volumetric changes of the structure within the three-dimensional cursor.

13. The method of claim 1 further comprising:
wherein said volume of said three-dimensional image is from a first imaging examination;
using the three-dimensional cursor for an additional imaging examination; and
registering a structure using registration markers within the three-dimensional cursor at the first imaging examination with the structure within the three-dimensional cursor of the additional imaging examination.

14. The method of claim 13 further comprising automatically calculating volumetric change of the structure based on the registration markers.

15. The method of claim 13 further comprising automatically re-orienting the selected volume based on the registration markers.

16. The method of claim 2 further comprising presenting the modified version of the selected volume inside the three-dimensional cursor in an augmented reality headset.

17. The method of claim 1 further comprising:
wherein the selecting is responsive to a user input; and
wherein the presenting is automatic.

18. The method of claim 1 further comprising:
wherein the selecting is responsive to a user input; and
wherein the presenting is responsive to said user input.

19. The method of claim 1 further comprising
wherein the selecting is automatic; and
wherein the presenting is automatic.

20. The method of claim 1 further comprising
wherein the selecting is automatic; and
wherein the presenting is responsive to said user input.

21. An apparatus comprising:
a headset;
a computing device; and
a human-machine interface comprising a three-dimensional cursor that has a non-zero volume;
the human-machine interface configured to select a three-dimensional image volume designated by the three-dimensional cursor, wherein the three-dimensional cursor encloses the selected volume responsive to an input; and
the human-machine interface configured to display the three-dimensional cursor including measurement markings that serve as constituent unit measurement indicators of a size of an element within the selected volume.

22. A non-transitory computer-readable medium storing instructions that, when executed, cause performance of:
generating a three-dimensional cursor that has a non-zero volume;
selecting a three-dimensional image volume designated by the three-dimensional cursor, wherein the three-dimensional cursor encloses the selected volume; and
displaying the three-dimensional cursor with measurement markings that serve as constituent unit measurement indicators of a size of an element within the selected volume.

23. The method of claim 1, wherein displaying comprises displaying the three-dimensional cursor with measurement markings on at least one edge, surface or side of the three-dimensional cursor.

24. The apparatus of claim 21, wherein displaying comprises displaying the three-dimensional cursor with measurement markings on at least one edge, surface or side of the three-dimensional cursor.

25. The computer-readable medium of claim 22, wherein displaying comprises displaying the three-dimensional cursor with measurement markings on at least one edge, surface or side of the three-dimensional cursor.

26. The computer-readable medium of claim 22, wherein the measurement markings enable a viewer to determine a total measurement of the selected volume.

27. The computer-readable medium of claim 22, wherein the measurement markings include first markings representing a first magnitude and second markings representing a second magnitude different from the first magnitude.

28. The computer-readable medium of claim 22, wherein the measurement markings serve as constituent unit measurement indicators of only a size of the three-dimensional cursor or one or more respective sizes of one or more elements within the cursor.

29. The computer-readable medium of claim 22, wherein the measurement markings serve as constituent unit measurement indicators of only one or more respective sizes of one or more elements within the cursor.

30. The computer-readable medium of claim 22, wherein the measurement markings are not placed outside the cursor.

* * * * *